(12) United States Patent
Kinsho et al.

(10) Patent No.: US 6,500,961 B2
(45) Date of Patent: Dec. 31, 2002

(54) LACTONE COMPOUNDS HAVING ALICYCLIC STRUCTURE AND THEIR MANUFACTURING METHOD

(75) Inventors: Takeshi Kinsho, Nakakubiki-gun (JP); Koji Hasegawa, Nakakubiki-gun (JP); Takeru Watanabe, Nakakubiki-gun (JP); Tsunehiro Nishi, Nakakubiki-gun (JP); Mutsuo Nakashima, Nakakubiki-gun (JP); Seiichiro Tachibana, Nakakubiki-gun (JP); Jun Hatakeyama, Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 9 days.

(21) Appl. No.: 09/867,656

(22) Filed: May 31, 2001

(65) Prior Publication Data

US 2002/0019545 A1 Feb. 14, 2002

(30) Foreign Application Priority Data

Jun. 1, 2000 (JP) .......................... 2000-164553

(51) Int. Cl.$^7$ .................... C07D 307/20; C07D 305/12; C07D 309/10; C07D 313/00
(52) U.S. Cl. ...................... 549/271; 549/273; 549/323; 549/328
(58) Field of Search ................. 549/271, 273, 549/323, 328

(56) References Cited

PUBLICATIONS

Kim et al., Polymer (2002), vol. 43, No. 6, pp. 1963–1967.*

* cited by examiner

*Primary Examiner*—T. A. Solola
(74) *Attorney, Agent, or Firm*—Millen, White, Zelano & Branigan, P.C.

(57) ABSTRACT

Lactone compounds of formula (1) are useful as monomers to form base resins for use in chemically amplified resist compositions adapted for micropatterning lithography.

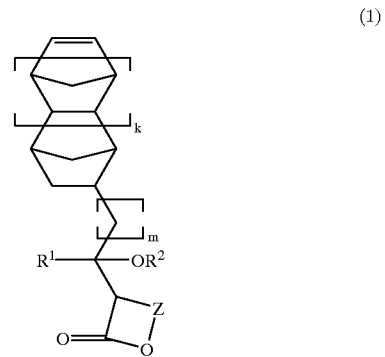

(1)

$R^1$ is H or $C_{1-6}$ alkyl, $R^2$ is H or an acyl or alkoxycarbonyl group of 1–15 carbon atoms which may be substituted with halogen atoms, Z is a divalent $C_{1-15}$ organic group which forms a lactone ring with the carbonyloxy group, k is 0 or 1, and m is an integer from 0 to 5.

3 Claims, No Drawings

LACTONE COMPOUNDS HAVING ALICYCLIC STRUCTURE AND THEIR MANUFACTURING METHOD

This invention relates to novel lactone compounds useful as monomers to form base resins for use in chemically amplified resist compositions adapted for micropatterning lithography, and a method for preparing the same.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 µm or less.

The resist materials for use in photolithography using light of an excimer laser, especially ArF excimer laser having a wavelength of 193 nm, are, of course, required to have a high transmittance to light of that wavelength. In addition, they are required to have an etching resistance sufficient to allow for film thickness reduction, a high sensitivity sufficient to eliminate any extra burden on the expensive optical material, and especially, a high resolution sufficient to form a precise micropattern. To meet these requirements, it is crucial to develop a base resin having a high transparency, rigidity and reactivity. None of the currently available polymers satisfy all of these requirements. Practically acceptable resist materials are not yet available.

Known high transparency resins include copolymers of acrylic or methacrylic acid derivatives and polymers containing in the backbone an alicyclic compound derived from a norbornene derivative. All these resins are unsatisfactory. For example, copolymers of acrylic or methacrylic acid derivatives are relatively easy to increase reactivity in that highly reactive monomers can be introduced and acid labile units can be increased as desired, but difficult to increase rigidity because of their backbone structure. On the other hand, the polymers containing an alicyclic compound in the backbone have rigidity within the acceptable range, but are less reactive with acid than poly(meth)acrylate because of their backbone structure, and difficult to increase reactivity because of the low freedom of polymerization. Additionally, since the backbone is highly hydrophobic, these polymers are less adherent when applied to substrates. Therefore, some resist compositions which are formulated using these polymers as the base resin fail to withstand etching although they have satisfactory sensitivity and resolution. Some other resist compositions are highly resistant to etching, but have low sensitivity and low resolution below the practically acceptable level.

SUMMARY OF THE INVENTION

An object of the invention is to provide a novel lactone compound useful as a monomer to form a polymer for use in the formulation of a photoresist composition which exhibits firm adhesion and high transparency when processed by photolithography using light with a wavelength of less than 300 nm, especially ArF excimer laser light as the light source. Another object is to provide a method for preparing the lactone compound.

We have found that a lactone compound of formula (1) can be prepared in high yields by a simple method, that a polymer obtained from this lactone compound has high transparency at the exposure wavelength of an excimer laser, and that a resist composition comprising the polymer as a base resin is improved in adhesion.

The invention provides a lactone compound of the following general formula (1).

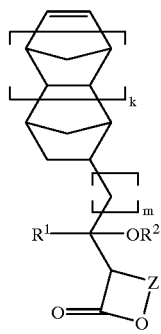

(1)

Herein $R^1$ is hydrogen or a straight, branched or cyclic alkyl group of 1 to 6 carbon atoms. $R^2$ is hydrogen or an acyl or alkoxycarbonyl group of 1 to 15 carbon atoms in which some or all of the hydrogen atoms on the constituent carbon atoms may be substituted with halogen atoms. Z is a divalent organic group of 1 to 15 carbon atoms which forms a lactone ring with the carbonyloxy group. The letter k is 0 or 1, and m is an integer from 0 to 5.

In another aspect, the invention provides a method for preparing a lactone compound of the following general formula (4), comprising effecting addition reaction of a metal enolate of the following general formula (3) to a carbonyl compound of the following general formula (2).

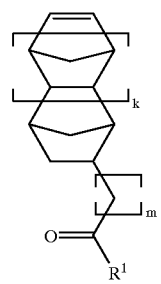

(2)

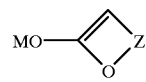

(3)

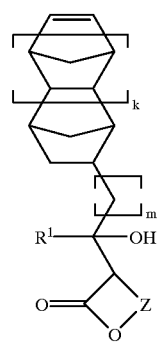

(4)

Herein k, m, $R^1$ and Z are as defined above, and M is Li, Na, K, MgY or ZnY wherein Y is a halogen atom.

In a further aspect, the invention provides a method for preparing a lactone compound of the following general formula (5), comprising subjecting to acylation or alkoxycarbonylation reaction the hydroxyl group on a compound of the following general formula (4).

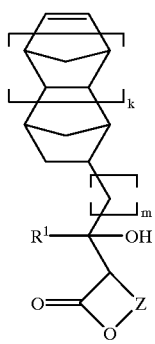

(4)

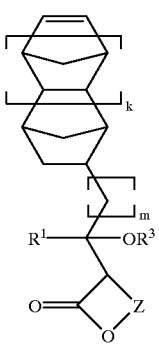

(5)

Herein k, m, $R^1$ and Z are as defined above, and $R^3$ is an acyl or alkoxycarbonyl group of 1 to 15 carbon atoms in which some or all of the hydrogen atoms on the constituent carbon atoms may be substituted with halogen atoms.

DESCRIPTION OF THE PREFERRED EMBODIMENT

The lactone compounds of the invention are of the following general formula (1).

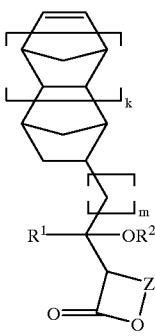

(1)

Herein $R^1$ is hydrogen or a straight, branched or cyclic alkyl group of 1 to 6 carbon atoms. Exemplary alkyl groups include methyl, ethyl, n-propyl, isopropyl, n-butyl, isobutyl, sec-butyl, tert-butyl, tert-amyl, n-pentyl, n-hexyl, cyclopentyl, and cyclohexyl.

$R^2$ is hydrogen or an acyl or alkoxycarbonyl group of 1 to 15 carbon atoms in which some or all of the hydrogen atoms on the constituent carbon atoms may be substituted with halogen atoms. Exemplary of $R^2$ are formyl, acetyl, propionyl, pivaloyl, methoxycarbonyl, ethoxycarbonyl, tert-butoxycarbonyl, trifluoroacetyl, trichloroacetyl, and 3,3,3-trifluoropropionyl.

Z is a divalent organic group of 1 to 15 carbon atoms which forms a lactone ring with the carbonyloxy group in formula (1). Specifically, the partial structure represented by

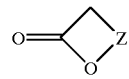

is exemplified by lactone structures represented by

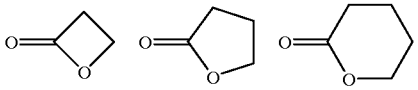

and structures having fused to these lactone structures a hydrocarbon ring (such as cycloalkane, cycloalkene or aromatic hydrocarbon) or a heterocyclic ring containing a hetero atom.

The letter k is 0 or 1, and m is an integer from 0 to 5 (i.e., $0 \leq m \leq 5$), and preferably from 0 to 3.

Illustrative, non-limiting, examples of the lactone compounds of formula (1) are given below.

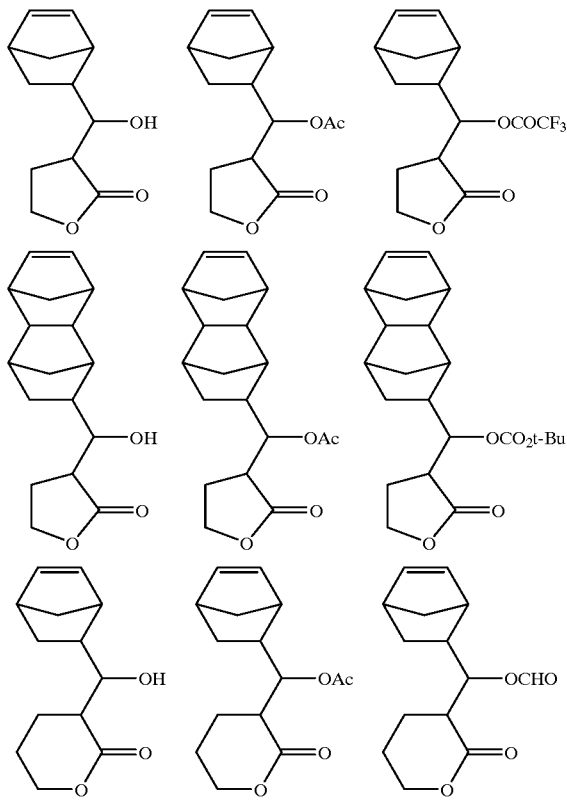

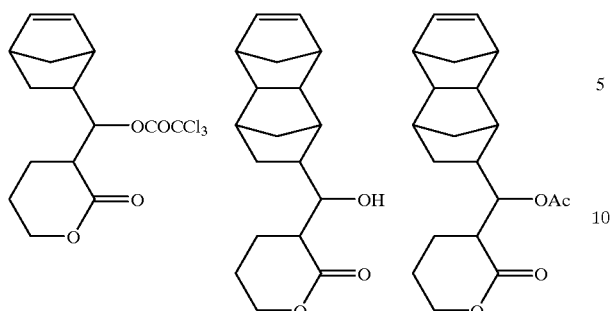

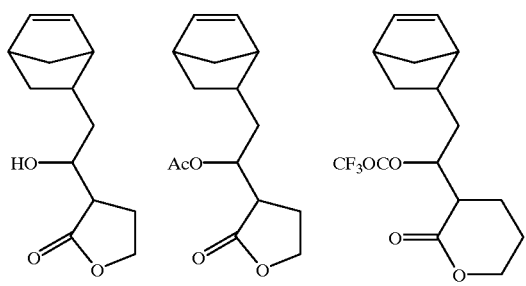

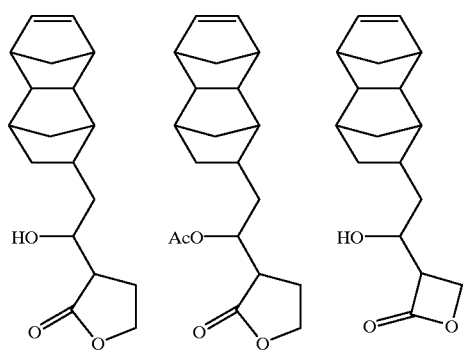

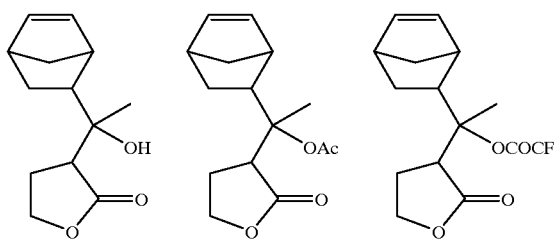

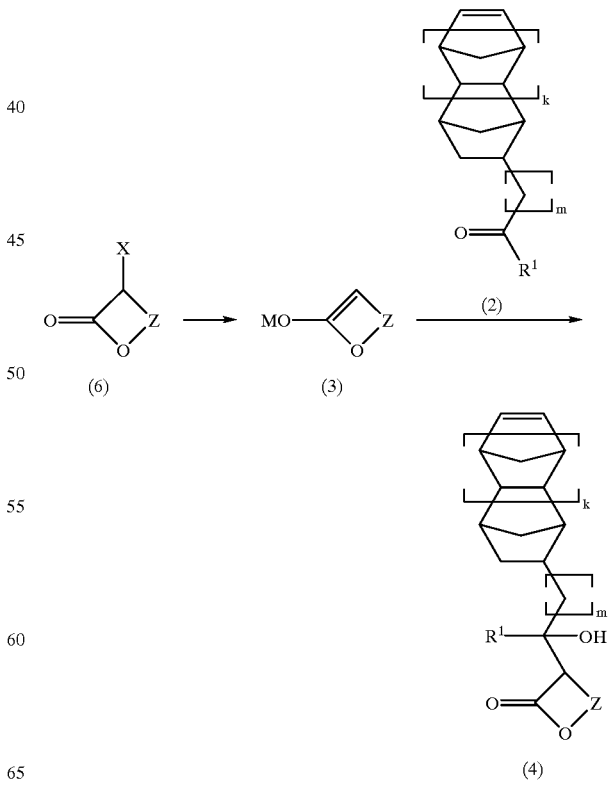

The inventive lactone compounds can be prepared, for example, by the following process, although the process is not limited thereto.

As seen from the reaction scheme shown below, the desired lactone compound can be prepared by the first step of treating a lactone compound of formula (6) with a base in a solvent in an inert gas atmosphere of nitrogen, argon or the like, forming a metal enolate of formula (3). The enolate solution is then reacted with a carbonyl compound of formula (2) to form a hydroxylactone compound of formula (4).

Preferably 0.8 to 2.0 mol, especially 1.0 to 1.5 mol of the base is used per mol of the lactone compound (6), and 0.8 to 2.0 mol, especially 0.9 to 1.5 mol of the carbonyl compound (2) is used per mol of the lactone compound (6).

Herein, k, m, R¹, R² and Z are as defined above, X is a hydrogen or halogen atom, M is Li, Na, K, MgY or ZnY wherein Y is a halogen atom.

When X is hydrogen, the bases used herein include metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and bromomagnesium diisopropylamide; alkoxides such as sodium methoxide, sodium ethoxide, lithium methoxide, lithium ethoxide, lithium tert-butoxide, and potassium tert-butoxide; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate and potassium carbonate; metal hydrides such as sodium hydride, lithium hydride, potassium hydride, and calcium hydride; and alkyl metal compounds such as trityl lithium, trityl sodium, trityl potassium, methyl lithium, phenyl lithium, sec-butyl lithium, tert-butyl lithium, and ethyl magnesium bromide. When X is halogen, the bases used herein include metals such as zinc and magnesium. The bases are not limited to these examples. Useful solvents are ethers such as tetrahydrofuran, diethyl ether, di-n-butyl ether, and 1,4-dioxane, hydrocarbons such as n-hexane, n-heptane, benzene, toluene, xylene and cumene, alcohols such as methanol, ethanol, isopropyl alcohol and tert-butyl alcohol, amines such as liquid ammonia and methyl amine, and aprotic polar solvents such as dimethyl sulfoxide and N,N-dimethylformamide. Any of these solvents may be selected depending on reaction conditions and used alone or in admixture thereof. A compound having a ligand such as N,N,N',N'-tetramethylethylenediamine (TMEDA), hexamethyl-phosphoric triamide (HMPA), N,N'-dimethylpropyleneurea (DMPU) or 1,3-dimethyl-2-imidazolidinone (DMI) may be used complementally.

The reaction temperature and time vary with particular starting reactants used. In one example where a lactone compound (6) wherein X is hydrogen and a strong base such as lithium bistrimethylsilylamide are used, the resulting metal enolate is thermally unstable, and the preferred conditions for reaction of the metal enolate with the carbonyl compound (2) include a reaction temperature in the low range of –80° C. to –20° C. and a reaction time of about ½ to about 3 hours. In another example where an α-halolactone compound (6) wherein X is halogen and a metal such as zinc are used, it is generally preferred to keep the reaction temperature in the range of 0 to 80° C. and the reaction time in the range of about 1 to 20 hours. The reaction conditions are not limited to these ranges. From the reaction mixture containing the nucleophilic addition product, the desired hydroxy compound (4) is obtained by a conventional aqueous work-up procedure. If necessary, the compound (4) is purified by any conventional technique such as distillation, chromatography or recrystallization.

By esterifying the hydroxy compound (4) thus obtained, a corresponding acyl or alkoxycarbonyl compound (5) is obtained.

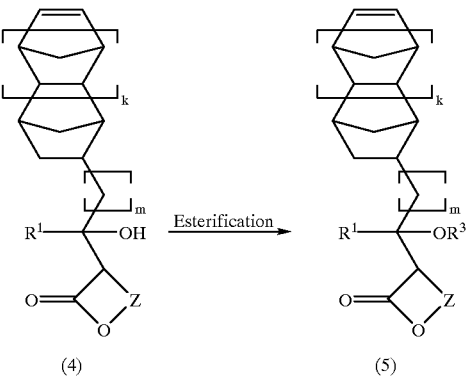

(4)                              (5)

Esterification may be carried out in a conventional way using 1 to 5 mol, preferably 1 to 2 mol of an esterifying agent per mol of the hydroxy compound (4). The esterifying agent is R³W wherein W stands for a hydroxyl group, halogen atom, acyloxy group, alkoxycarbonyloxy group, or an eliminatable group such as p-nitrophenyloxy. Examples of the esterifying agent R³W include carboxylic acids such as formic acid (where W=OH), acid halides such as acetyl chloride, acetyl bromide and propionyl chloride (where W=halogen), acid anhydrides such as acetic anhydride, trifluoroacetic anhydride, mixed acid anhydride of formic acid/acetic acid, and di-t-butyl dicarbonate (where W=acyloxy or alkoxycarbonyloxy), and activated esters such as p-nitrophenyl acetate and p-nitrophenyl propionate (where W=eliminatable group such as p-nitrophenyloxy). The reaction may be carried out in a solventless system or in a suitable solvent selected from among chlorinated solvents such as methylene chloride, chloroform, trichlene; ethers such as tetrahydrofuran, diethyl ether, di-n-butyl ether, and 1,4-dioxane; and hydrocarbons such as n-hexane, n-heptane, benzene, toluene, xylene and cumene, alone or in admixture of any. Except the case wherein the esterifying agent is a carboxylic acid (W=OH), it is desirable to use a base in an amount of 1 to 30 mol, especially 1 to 5 mol per mol of the hydroxy compound (4). Exemplary bases are triethylamine, pyridine, dimethylaniline, and 4-dimethylaminopyridine, which may be used alone or in admixture. The reaction is carried out by adding the esterifying agent and the base sequentially or simultaneously while heating or cooling the system if necessary. The reaction yields a reaction mixture containing the esterified product. The desired ester compound (5) is separated from the reaction mixture by a conventional aqueous work-up procedure. If necessary, the compound (5) is purified by any conventional technique such as distillation, chromatography or recrystallization.

A polymer is prepared using the inventive lactone compound as a monomer. The method is generally by mixing the monomer with a solvent, adding a catalyst or polymerization initiator, and effecting polymerization reaction while heating or cooling the system if necessary. This polymerization reaction can be effected in a conventional way.

A resist composition is formulated using as a base resin the polymer resulting from polymerization of the lactone compound. Usually, the resist composition is formulated by adding an organic solvent and a photoacid generator to the polymer and if necessary, further adding a crosslinker, a basic compound, a dissolution inhibitor and other additives. Preparation of the resist composition can be effected in a conventional way.

The resist composition formulated using the polymer resulting from polymerization of the inventive lactone compound lends itself to micropatterning with electron beams or deep-UV rays since it is sensitive to high-energy radiation and has excellent sensitivity, resolution, and etching resistance. Especially because of the minimized absorption at the exposure wavelength of an ArF or KrF excimer laser and firm adhesion to the substrate, a finely defined pattern having sidewalls perpendicular to the substrate can easily be formed. The resist composition is thus suitable as micropatterning material for VLSI fabrication.

EXAMPLE

Synthesis Examples and Reference Examples are given below for further illustrating the invention. It is not construed that the invention be limited to these examples.

Synthesis Examples are first described. Lactone compounds within the scope of the invention were synthesized in accordance with the following formulation.

Synthesis Example 1

Synthesis of α-[hydroxy(5-norbornen-2-yl)methyl]-γ-butyrolactone (Monomer 1)

First, in a nitrogen atmosphere, 184 g of lithium bis(trimethylsilyl)amide and 86 g of γ-butyrolactone were reacted in 1 kg of dry tetrahydrofuran at −60° C. to form lithium enolate. Then 122 g of 5-norbornene-2-carbaldehyde was slowly added, following which the temperature was raised to −20° C. over one hour, at which reaction was effected. Then 1 kg of a saturated ammonium chloride aqueous solution was added to stop the reaction, whereupon hexane was added for extraction. The organic layer was washed with water, dried over anhydrous sodium sulfate, filtered, and concentrated in vacuum. Purification by silica gel column chromatography yielded 198 g (yield 95%) of α-[hydroxy(5-norbornen-2-yl)methyl]-γ-butyrolactone, designated Monomer 1.

IR (KBr): ν=3436 (br.), 3058, 2966, 2867, 1740, 1385, 1336, 1219, 1184, 1024 cm$^{-1}$ $^1$H-NMR of main diastereomer (270 MHz in CDCl$_3$): δ=0.52 (1H, m), 1.20–1.45 (2H, m), 1.55–3.25 (9H, m), 4.30–4.45 (2H, m), 6.02 (1H, m), 6.20 (1H, m) ppm.

Synthesis Example 2

Synthesis of α-[hydroxy(5-norbornen-2-yl)methyl]-γ-butyrolactone (Monomer 1)

Addition reaction was carried out by mixing 98 g of zinc powder, 247 g of α-bromo-γ-butyrolactone, 122 g of 5-norbornene-2-carbaldehyde, and 2 kg of dry tetrahydrofuran and heating the mixture under reflux for 10 hours in a nitrogen atmosphere. The reaction mixture was cooled, to which dilute hydrochloric acid was added for neutralization and hexane was added for extraction. The organic layer was washed with water, dried over anhydrous sodium sulfate, filtered, and concentrated in vacuum. Purification by silica gel column chromatography yielded 148 g (yield 71%) of α-[hydroxy(5-norbornen-2-yl)methyl]-γ-butyrolactone.

Synthesis Example 3

Synthesis of α-[acetoxy(5-norbornen-2-yl)methyl]-γ-butyrolactone (Monomer 2)

To the mixture of 208 g of α-[hydroxy(5-norbornen-2-yl)methyl]-γ-butyrolactone (Monomer 1), 127 g of pyridine and 6 g of 4-dimethylaminopyridine was added dropwise 123 g of acetic anhydride. Reaction was effected at 25° C. for 10 hours. Water, 30 g, was added to the reaction mixture to stop reaction, followed by hexane extraction. The organic layer was washed with water, dried over anhydrous sodium sulfate, filtered, and concentrated in vacuum. Purification by silica gel column chromatography yielded 245 g (yield 98%) of α-[acetoxy(5-norbornen-2-yl)methyl]-γ-butyrolactone.

IR (KBr): ν=3061, 2974, 2870, 1761, 1728, 1375, 1244, 1161, 1153, 1026 cm$^{-1}$ $^1$H-NMR of main diastereomer (270 MHz in CDCl$_3$): δ=0.58 (1H, ddd, J=11.6, 4.9, 2.4 Hz), 1.30 (1H, m), 1.41 (1H, m), 1.70–2.50 {(6H, m) including 2.11 (3H, s)}, 2.55–3.05 (4H, m), 4.05–4.30 (2H, m), 4.60 (1H, dd, J=11.1, 2.4 Hz), 5.87 (1H, m), 6.18 (1H, m) ppm.

Synthesis Example 4

Synthesis of α-[1-hydroxy-2-(5-norbornen-2-yl)ethyl]-γ-butyrolactone (Monomer 3)

The procedure of Synthesis Example 1 was repeated except that (5-norbornen-2-yl)acetaldehyde was used instead of 5-norbornene-2-carbaldehyde, synthesizing α-[1-hydroxy-2-(5-norbornen-2-yl)ethyl]-γ-butyrolactone in a yield of 93%.

IR (KBr): ν=3404 (br.), 3057, 2962, 2937, 2866, 1749, 1380, 1213, 1178, 1024 cm$^{-1}$ $^1$H-NMR of main diastereomer (270 MHz in CDCl$_3$): δ=0.51 (1H, m), 0.95–2.90 (12H, m), 3.67 (1H, ddd, J=10.0, 7.8, 2.7 Hz), 4.10–4.30 (2H, m), 5.92 (1H, m), 6.12 (1H, m) ppm.

Synthesis Example 5

Synthesis of α-[1-acetoxy-2-(5-norbornen-2-yl)ethyl]-γ-butyrolactone (Monomer 4)

The procedure of Synthesis Example 3 was repeated except that α-[1-hydroxy-2-(5-norbornen-2-yl)ethyl]-γ-butyrolactone (Monomer 3) was used instead of α-[hydroxy(5-norbornen-2-yl)methyl]-γ-butyrolactone (Monomer 1), synthesizing α-[1-acetoxy-2-(5-norbornen-2-yl)ethyl]-γ-butyrolactone in a yield of 98%.

IR (thin film): ν=3057, 2964, 2868, 1772, 1738, 1373, 1238, 1171, 1161, 1026 cm$^{-1}$ $^1$H-NMR of main diastereomer (270 MHz in CDCl$_3$): δ=0.55 (1H, m), 1.15–2.95 {(14H, m) including 2.07 (3H, s)}, 4.10–4.40 (2H, m), 5.36 (1H, m), 5.93 (1H, m), 6.11 (1H, m) ppm.

The structural formulas of Monomers 1 to 4 are shown below.

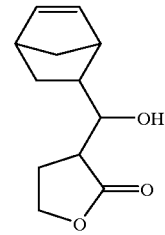

monomer 1

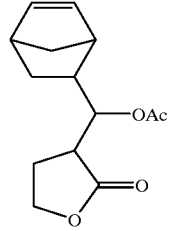

monomer 2 monomer 3

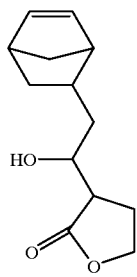

monomer 4

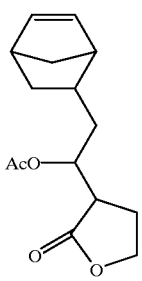

Reference Example

Polymers were synthesized using the lactone compounds obtained in the above Synthesis Examples. Using the polymers as a base resin, resist compositions were formulated, which were examined for substrate adhesion.

Polymerization reaction of tert-butyl 5-norbornene-2-carboxylate, Monomer 1, and maleic anhydride was effected using 2,2'-azobis(2,4-dimethylvaleronitrile) as the initiator, yielding an alternating copolymer of tert-butyl 5-norbornene-2-carboxylate/α-[hydroxy(5-norbornen-2-yl)methyl]-γ-butyrolactone/maleic anhydride (copolymerization ratio 4/1/5).

A resist composition was prepared by blending 80 parts by weight of the above copolymer as a base resin, 1.0 part by weight of triphenylsulfonium trifluoromethanesulfonate as a photoacid generator, 480 parts by weight of propylene glycol monomethyl ether acetate as a solvent, and 0.08 part by weight of tributylamine. The composition was spin coated on a silicon wafer having hexamethyldisilazane sprayed thereon at 90° C. for 40 seconds and heat treated at 110° C. for 90 seconds, forming a resist film of 500 nm thick. The resist film was exposed to KrF excimer laser light, heat treated at 110° C. for 90 seconds, and developed by immersing in a 2.35% tetramethylammonium hydroxide aqueous solution for 60 seconds, thereby forming a 1:1 line-and-space pattern. The wafer as developed was observed under SEM, finding that the pattern down to 0.26 μm size was left unstrapped.

Comparative Reference Example

For comparison purposes, a resist composition was prepared as above, using an alternating copolymer of tert-butyl 5-norbornene-2-carboxylate/maleic anhydride (copolymerization ratio 1/1). It was similarly processed, and examined for substrate adhesion. No patterns with a size of 0.50 μm or less were left.

It was confirmed that polymers resulting from the inventive lactone compounds have significantly improved substrate adhesion as compared with prior art polymers.

Japanese Patent Application No. 2000-164553 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A lactone compound of the following general formula (1):

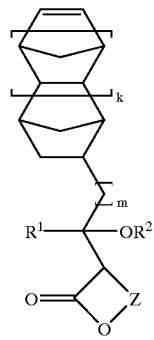

(1)

wherein $R^1$ is hydrogen or a straight, branched or cyclic alkyl group of 1 to 6 carbon atoms, $R^2$ is hydrogen or an acyl or alkoxycarbonyl group of 1 to 15 carbon atoms in which some or all of the hydrogen atoms on the constituent carbon atoms may be substituted with halogen atoms, Z is a divalent organic group of 1 to 15 carbon atoms which forms a lactone ring with the carbonyloxy group, k is 0 or 1, and m is an integer from 0 to 5.

2. A method for preparing a lactone compound of the following general formula (4), comprising effecting addition reaction of a metal enolate of the following general formula (3) to a carbonyl compound of the following general formula (2):

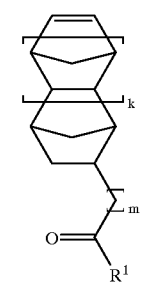

(2)

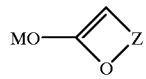

(3)

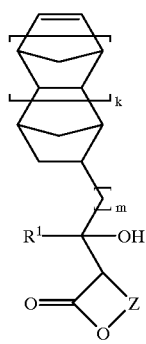

(4)

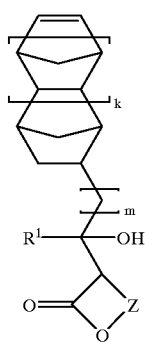

(4)

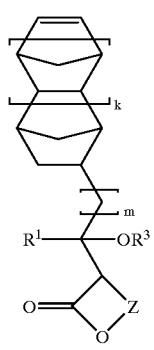

(5)

wherein $R^1$ is hydrogen or a straight, branched or cyclic alkyl group of 1 to 6 carbon atoms, Z is a divalent organic group of 1 to 15 carbon atoms which forms a lactone ring with the carbonyloxy group, k is 0 or 1, m is an integer from 0 to 5, and M is Li, Na, K, MgY or ZnY wherein Y is a halogen atom.

3. A method for preparing a lactone compound of the following general formula (5), comprising subjecting to acylation or alkoxycarbonylation reaction the hydroxyl group on a compound of the following general formula (4):

wherein $R^1$ is hydrogen or a straight, branched or cyclic alkyl group of 1 to 6 carbon atoms, Z is a divalent organic group of 1 to 15 carbon atoms which forms a lactone ring with the carbonyloxy group, k is 0 or 1, m is an integer from 0 to 5, and $R^3$ is an acyl or alkoxycarbonyl group of 1 to 15 carbon atoms in which some or all of the hydrogen atoms on the constituent carbon atoms may be substituted with halogen atoms.

* * * * *